(12) United States Patent
Verleur et al.

(10) Patent No.: US 10,779,576 B2
(45) Date of Patent: Sep. 22, 2020

(54) FLAVOR DISK

(71) Applicant: VMR Products LLC, Miami, FL (US)

(72) Inventors: Jan Andries Verleur, Miami Beach, FL (US); Dan Recio, Miami Beach, FL (US); Zhiyuan Liu, Miami, FL (US); Hans Verleur, El Dorado, CA (US)

(73) Assignee: VMR Products, LLC, San Francisco, CA (US)

( * ) Notice: Subject to any disclaimer, the term of this patent is extended or adjusted under 35 U.S.C. 154(b) by 90 days.

(21) Appl. No.: 15/987,702

(22) Filed: May 23, 2018

(65) Prior Publication Data

US 2018/0338532 A1  Nov. 29, 2018

Related U.S. Application Data

(60) Provisional application No. 62/510,484, filed on May 24, 2017.

(51) Int. Cl.
| | | |
|---|---|---|
| *A24F 47/00* | (2020.01) | |
| *A61M 15/06* | (2006.01) | |
| *A61M 11/04* | (2006.01) | |
| *A24B 15/167* | (2020.01) | |
| *A61M 15/00* | (2006.01) | |

(52) U.S. Cl.
CPC .......... *A24F 47/008* (2013.01); *A24B 15/167* (2016.11); *A61M 11/042* (2014.02); *A61M 15/06* (2013.01); *A61M 15/0021* (2014.02); *A61M 15/0028* (2013.01); *A61M 2205/3653* (2013.01); *A61M 2205/50* (2013.01); *A61M 2205/8206* (2013.01)

(58) Field of Classification Search
CPC .................................................... A24F 47/008
See application file for complete search history.

(56) References Cited

U.S. PATENT DOCUMENTS

| | | | |
|---|---|---|---|
| 5,649,554 A | * | 7/1997 | Sprinkel ............... A24F 47/008 128/202.21 |
| 5,792,057 A | | 8/1998 | Rubsamen et al. |
| 8,156,944 B2 | | 4/2012 | Han |
| 8,881,737 B2 | | 11/2014 | Collett et al. |
| 8,910,640 B2 | | 12/2014 | Sears et al. |
| 8,991,402 B2 | | 3/2015 | Bowen et al. |

(Continued)

FOREIGN PATENT DOCUMENTS

| | | |
|---|---|---|
| AT | 507187 A4 | 3/2010 |
| AU | 2014208287 B2 | 12/2016 |

(Continued)

*Primary Examiner* — Michael H. Wilson
*Assistant Examiner* — Jennifer A Kessie
(74) *Attorney, Agent, or Firm* — MIntz Levin Cohn Ferris Glovsky and Popeo, P.C.

(57) ABSTRACT

A flavor disk for use in a vaporizer is disclosed. The flavor disk may include a plurality of chambers, each chamber storing a flavor component. The flavor disk may further include an actuator for each chamber, the actuator configured to selectively release a portion of the flavor component from the chamber. The flavor disk may further include a flow path positioned to receive the portion of the flavor component and mix the portion of the flavor component with incoming fluid. The flavor disk may further include control circuitry for actuating the actuator.

15 Claims, 3 Drawing Sheets

(56) References Cited

U.S. PATENT DOCUMENTS

| | | |
|---|---|---|
| 9,271,529 B2 | 3/2016 | Alima |
| 9,408,416 B2 | 8/2016 | Monsees et al. |
| 9,609,895 B2 | 4/2017 | Galloway et al. |
| 9,629,391 B2 | 4/2017 | Dube et al. |
| 9,675,109 B2 | 6/2017 | Monsees et al. |
| 9,682,204 B2 | 6/2017 | Matsumoto et al. |
| 9,738,622 B2 | 8/2017 | Dull et al. |
| 9,763,478 B2 | 9/2017 | Cameron et al. |
| 9,770,055 B2 | 9/2017 | Cameron et al. |
| 10,045,567 B2 | 8/2018 | Monsees et al. |
| 10,058,128 B2 | 8/2018 | Cameron et al. |
| 10,058,130 B2 | 8/2018 | Monsees et al. |
| 10,080,387 B2 | 9/2018 | Phillips et al. |
| 10,085,486 B2 | 10/2018 | Cameron |
| 10,143,242 B2 | 12/2018 | Weigensberg et al. |
| 10,231,484 B2 | 3/2019 | Bowen et al. |
| 10,244,793 B2 | 4/2019 | Monsees et al. |
| 10,292,427 B2 | 5/2019 | Cameron et al. |
| 2007/0098148 A1 | 5/2007 | Sherman |
| 2009/0192443 A1 | 7/2009 | Collins, Jr. |
| 2013/0174842 A1 | 7/2013 | Young et al. |
| 2013/0255675 A1 | 10/2013 | Liu |
| 2013/0255702 A1 | 10/2013 | Griffith, Jr. et al. |
| 2013/0276799 A1 | 10/2013 | Davidson et al. |
| 2013/0306065 A1 | 11/2013 | Thorens et al. |
| 2013/0312742 A1 | 11/2013 | Monsees et al. |
| 2014/0000638 A1 | 1/2014 | Sebastian et al. |
| 2014/0041655 A1 | 2/2014 | Barron et al. |
| 2014/0158129 A1 | 6/2014 | Pratt, Jr. et al. |
| 2014/0166029 A1 | 6/2014 | Weigensberg et al. |
| 2014/0202454 A1 | 7/2014 | Buchberger |
| 2014/0238421 A1 | 8/2014 | Shapiro |
| 2014/0253144 A1 | 9/2014 | Novak, III et al. |
| 2014/0261487 A1 | 9/2014 | Chapman et al. |
| 2014/0366898 A1 | 12/2014 | Monsees et al. |
| 2015/0217068 A1 | 8/2015 | Wakalopulos |
| 2015/0313283 A1 | 11/2015 | Collett et al. |
| 2016/0128389 A1 | 5/2016 | Lamb et al. |
| 2016/0158782 A1 | 6/2016 | Henry, Jr. et al. |
| 2016/0219933 A1 | 8/2016 | Henry, Jr. et al. |
| 2016/0235124 A1 | 8/2016 | Krietzman |
| 2016/0261021 A1 | 9/2016 | Marion et al. |
| 2016/0262454 A1* | 9/2016 | Sears .................. A24F 47/008 |
| 2016/0262459 A1 | 9/2016 | Monsees et al. |
| 2016/0295922 A1 | 10/2016 | John et al. |
| 2016/0324217 A1 | 11/2016 | Cameron |
| 2016/0325055 A1 | 11/2016 | Cameron |
| 2016/0331022 A1 | 11/2016 | Cameron |
| 2016/0331023 A1 | 11/2016 | Cameron |
| 2016/0331024 A1 | 11/2016 | Cameron |
| 2016/0331025 A1 | 11/2016 | Cameron |
| 2016/0331026 A1 | 11/2016 | Cameron |
| 2016/0331027 A1 | 11/2016 | Cameron |
| 2016/0331034 A1 | 11/2016 | Cameron |
| 2016/0331037 A1 | 11/2016 | Cameron |
| 2016/0334847 A1 | 11/2016 | Cameron |
| 2016/0337141 A1 | 11/2016 | Cameron |
| 2016/0337362 A1 | 11/2016 | Cameron |
| 2016/0337444 A1 | 11/2016 | Cameron |
| 2016/0345631 A1 | 12/2016 | Monsees et al. |
| 2016/0356751 A1 | 12/2016 | Blackley |
| 2016/0360785 A1 | 12/2016 | Bless et al. |
| 2016/0363570 A1 | 12/2016 | Blackley |
| 2016/0363917 A1 | 12/2016 | Blackley |
| 2016/0367925 A1 | 12/2016 | Blackley |
| 2016/0370335 A1 | 12/2016 | Blackley |
| 2016/0374400 A1 | 12/2016 | Monsees et al. |
| 2017/0013880 A1 | 1/2017 | O'Brien et al. |
| 2017/0018000 A1 | 1/2017 | Cameron |
| 2017/0020188 A1 | 1/2017 | Lamb et al. |
| 2017/0020191 A1 | 1/2017 | Lamb et al. |
| 2017/0020195 A1 | 1/2017 | Cameron |
| 2017/0020196 A1 | 1/2017 | Cameron |
| 2017/0020197 A1 | 1/2017 | Cameron |
| 2017/0023952 A1 | 1/2017 | Henry, Jr. et al. |
| 2017/0027229 A1 | 2/2017 | Cameron |
| 2017/0042230 A1 | 2/2017 | Cameron |
| 2017/0042231 A1 | 2/2017 | Cameron |
| 2017/0046357 A1 | 2/2017 | Cameron |
| 2017/0046738 A1 | 2/2017 | Cameron |
| 2017/0055588 A1 | 3/2017 | Cameron |
| 2017/0071249 A1 | 3/2017 | Ampolini et al. |
| 2017/0079331 A1 | 3/2017 | Monsees et al. |
| 2017/0086496 A1 | 3/2017 | Cameron |
| 2017/0086497 A1 | 3/2017 | Cameron |
| 2017/0086503 A1 | 3/2017 | Cameron |
| 2017/0086504 A1 | 3/2017 | Cameron |
| 2017/0091853 A1 | 3/2017 | Cameron |
| 2017/0092106 A1 | 3/2017 | Cameron |
| 2017/0093960 A1 | 3/2017 | Cameron |
| 2017/0093981 A1 | 3/2017 | Cameron |
| 2017/0112190 A1 | 4/2017 | Buchberger |
| 2017/0119052 A1 | 5/2017 | Williams et al. |
| 2017/0119053 A1 | 5/2017 | Henry, Jr. et al. |
| 2017/0119058 A1 | 5/2017 | Cameron |
| 2017/0135407 A1 | 5/2017 | Cameron |
| 2017/0135408 A1 | 5/2017 | Cameron |
| 2017/0135409 A1 | 5/2017 | Cameron |
| 2017/0135411 A1 | 5/2017 | Cameron |
| 2017/0135412 A1 | 5/2017 | Cameron |
| 2017/0136193 A1 | 5/2017 | Cameron |
| 2017/0136194 A1 | 5/2017 | Cameron |
| 2017/0136196 A1 | 5/2017 | Davidson et al. |
| 2017/0136301 A1 | 5/2017 | Cameron |
| 2017/0156397 A1 | 6/2017 | Sur et al. |
| 2017/0156398 A1 | 6/2017 | Sur et al. |
| 2017/0170439 A1 | 6/2017 | Jarvis et al. |
| 2017/0181223 A1 | 6/2017 | Sur et al. |
| 2017/0181474 A1 | 6/2017 | Cameron |
| 2017/0181475 A1 | 6/2017 | Cameron |
| 2017/0185364 A1 | 6/2017 | Cameron |
| 2017/0188627 A1 | 7/2017 | Sur |
| 2017/0188635 A1 | 7/2017 | Force et al. |
| 2017/0196263 A1 | 7/2017 | Sur |
| 2017/0208863 A1 | 7/2017 | Davis et al. |
| 2017/0215473 A1 | 8/2017 | Nakano et al. |
| 2017/0251724 A1 | 9/2017 | Lamb et al. |
| 2017/0290371 A1 | 10/2017 | Davis et al. |
| 2018/0037381 A1 | 2/2018 | White et al. |
| 2018/0064174 A1 | 3/2018 | Monsees et al. |
| 2018/0140015 A1 | 5/2018 | Carroll et al. |
| 2018/0338532 A1 | 11/2018 | Verleur et al. |
| 2019/0069598 A1 | 3/2019 | Liu |
| 2019/0124982 A1 | 5/2019 | Atkins et al. |
| 2019/0223510 A1 | 7/2019 | Bowen et al. |

FOREIGN PATENT DOCUMENTS

| | | |
|---|---|---|
| CA | 2729601 C | 9/2013 |
| CN | 1233436 A | 11/1999 |
| CN | 101557728 B | 4/2011 |
| CN | 203597403 U | 5/2014 |
| CN | 103929988 B | 4/2016 |
| EP | 2789250 A2 | 10/2014 |
| EP | 2768327 B1 | 3/2016 |
| EP | 3061359 B1 | 10/2018 |
| EP | 3117860 B1 | 1/2019 |
| EP | 3250059 B1 | 6/2019 |
| EP | 3248483 B1 | 9/2019 |
| KR | 101611783 B1 | 4/2016 |
| KR | 101979051 B1 | 5/2019 |
| WO | WO-2009079641 A2 | 6/2009 |
| WO | WO-2012134117 A2 | 10/2012 |
| WO | WO-2013113612 A1 | 8/2013 |
| WO | WO-2016015247 A1 | 2/2016 |
| WO | WO-2016055653 A1 | 4/2016 |
| WO | WO-2016169019 A1 | 10/2016 |
| WO | WO-2016178098 A2 | 11/2016 |
| WO | WO-2017045897 A1 | 3/2017 |
| WO | WO-2017089931 A1 | 6/2017 |
| WO | WO-2017205838 A1 | 11/2017 |

* cited by examiner

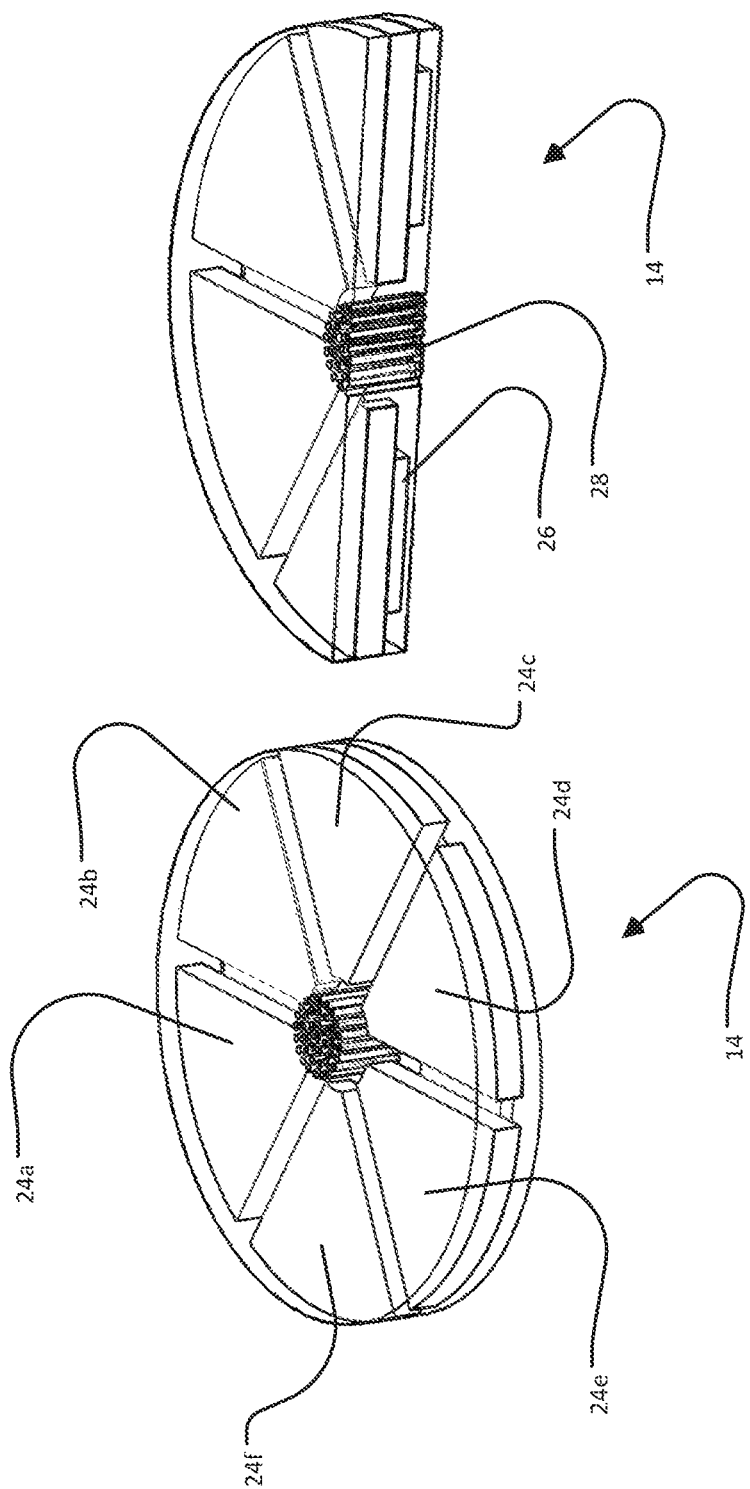

FLAVOR DISK

CROSS REFERENCE TO RELATED APPLICATIONS

This application claims the benefit of U.S. Provisional Application Ser. No. 62/510,484 filed May 24, 2017, the disclosure of which is hereby incorporated herein by reference in its entirety.

BACKGROUND

1. Technical Field

This disclosure relates generally to vaporizers, and more particularly to a flavor disk for a vaporizer.

2. Background Information

Vaporizers have recently emerged as a new product for providing nicotine and other products through a smokeless inhalation process. There are many embodiments of vaporizers including the electronic cigarette. Most implementations consist of a power supply (typically a battery) and an atomizing device. In reusable electronic cigarettes the two items are separated into a battery and a cartomizer, to allow the disposal and replacement of the nicotine containing fluid cartomizer while preserving the more costly battery and associated circuitry (microcontroller, switch, indicating LED, etc.) In disposable electronic cigarettes the two items are combined to integrate the functions into one unit that is disposed of after either the battery energy or the nicotine containing E-liquid is exhausted.

The E-liquid that is used to produce vapor in electronic cigarettes is generally a solution of one or more of propylene glycol (PG) and/or vegetable glycerin (VG) and/or polyethylene glycol 400 (PEG400) mixed with concentrated flavors, and optionally, a variable percentage of a liquid nicotine concentrate. This liquid may be termed an "E-liquid" and is often sold in a bottle or in disposable cartridges or cartomizers. Many different flavors of such E-liquids are sold, including flavors that resemble the taste of regular tobacco, menthol, vanilla, coffee, cola and various fruits. Various nicotine concentrations are also available, and nicotine-free E-Liquids are common.

BRIEF SUMMARY

In one aspect of the disclosure, a flavor disk for use in a vaporizer is disclosed. The flavor disk may include a plurality of chambers, each chamber storing a flavor component. The flavor disk may further include an actuator for each chamber, the actuator configured to selectively release a portion of a flavor component from a chamber. The flavor disk may further include a flow path positioned to receive the portion of a flavor component and mix the portion of a flavor component with incoming fluid. The flavor disk may further include control circuitry for actuating the actuator. Upon the control circuitry actuating the actuator, flavor from the flavor disk may be introduced into the flow path to mix with incoming fluid. The flavor may additionally be mixed with vapor produced by a vapor source.

In a second aspect of the disclosure, a vaporizer assembly is disclosed. The vaporizer assembly may include a flavor disk and a vaporizer. The flavor disk may include a plurality of chambers, each chamber storing a flavor component. The flavor disk may further include a respective actuator for each chamber, each actuator independently configured to selectively release a portion of the stored flavor component. The flavor disk may further include a flow path positioned to receive the portion of a flavor component and mix the portion of a flavor component with incoming fluid. The flavor disk may further include control circuitry for actuating the actuator(s). The vaporizer may be configured to receive the flavor disk. The vaporizer may further define a space configured to receive, from the flavor disk, the portion of a flavor component that is mixed with the incoming fluid. The space may further be configured to mix vapor produced by the vaporizer with the portion of a flavor component that is mixed with the incoming fluid.

BRIEF DESCRIPTION OF THE DRAWINGS

FIG. 2 illustrates a perspective view of a flavor disk.

FIG. 3 illustrates a sectional view of the flavor disk of FIG. 2.

DETAILED DESCRIPTION

The following detailed description and the appended drawings describe and illustrate some embodiments of the disclosure for the purpose of enabling one of ordinary skill in the relevant art to make and use these embodiments. As such, the detailed description and illustration of these embodiments are purely illustrative in nature and are in no way intended to limit the scope of the disclosure in any manner. It should also be understood that the drawings are not necessarily to scale and in certain instances details may have been omitted, which are not necessary for an understanding of the embodiments, such as details of fabrication and assembly. In the accompanying drawings, like numerals represent like components.

Figure 1:
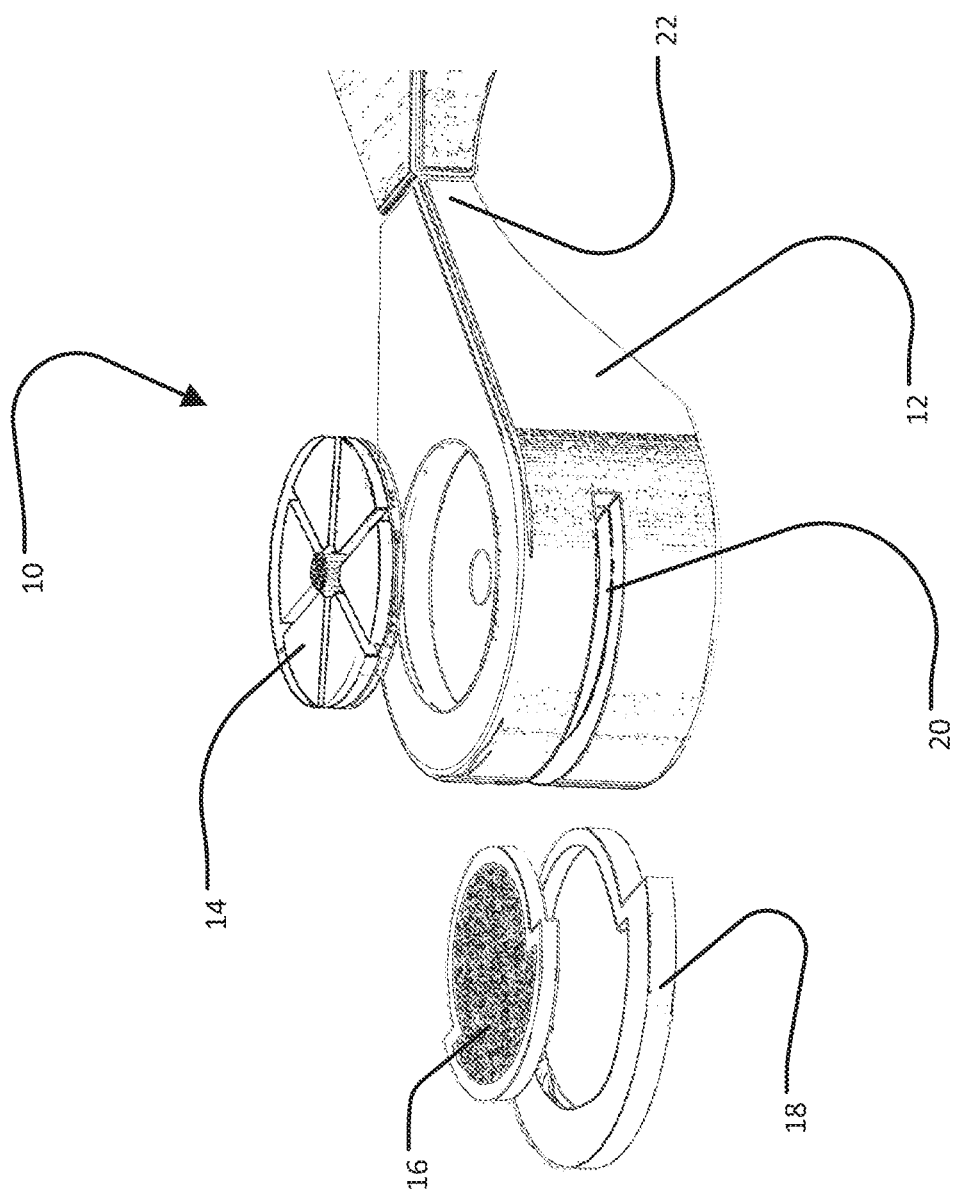
FIG. 1 illustrates an exploded view of an embodiment vaporizer assembly having a flavor disk.

FIG. 1 illustrates an exploded view of a vaporizer assembly 10. The vaporizer assembly 10 includes a vaporizer 12, a flavor disk 14, a vaporizer product 16, and a tray 18. Vaporizer 12 has a slot 20 sized and shaped to receive tray 18. Tray 18 has a cavity sized and shaped to receive vaporizer product 16. Tray 18 is removed from vaporizer 12 to load vaporizer product 16 into tray 18, which may then be inserted into slot 20 to load vaporizer product 16 into vaporizer 12. Flavor disk 14 may be removable from vaporizer 12 to load flavors into flavor disk 14, or to replace a used flavor disk with a new flavor disk. In some embodiments, flavor disk 14 may not be detachable from the vaporizer, such that reloading flavors must be performed directly into vaporizer assembly 10. In other embodiments, the flavors may be non-replaceable.

Vaporizer 12 has a mouthpiece 22 opposite slot 20. A user inhales vapors produced by the vaporizer 12 at mouthpiece 22. Although mouthpiece 22 is shown as a relatively short mouthpiece 22 in the embodiment of FIG. 1, mouthpiece 22 may be of varying lengths. Additionally, mouthpiece 22 may be configured to connect to a mouthpiece extension depending on user preference. For example, a mouthpiece extension could have a length and internal diameter selected by a user. A mouthpiece extension having a smaller internal diameter extension may have a greater flow restriction, which may be preferable to some users.

FIG. 2 illustrates a flavor disk 14 for use in the vaporizer 12 of FIG. 1. FIG. 3 illustrates a cross section of the flavor disk 14 of FIG. 1. Flavor disk 14 contains individual flavors that may be mixed with vapor to produce a flavored vapor. Flavor disk 14 may have multiple flavors to allow a user to select a flavor according to their mood or preference. For example, the embodiment of FIG. 2 has six different chambers 24 a-f with each of chambers 24 a-f potentially storing a different respective flavor. In some embodiments, a flavor may be present in more than one of chambers 24 a-f. For example, although six chambers 24 a-f are present in the embodiment of FIG. 2, there may be three different flavors with each flavor being present in two of chambers 24 a-f. Although exemplary flavor disk 14 is depicted as including six chambers 24 a-f, flavor disks according to this disclosure may include any suitable number of chambers, which may include more or less than six chambers.

Flavor disk 14 has an electrical connector for providing electrical communication to a control panel of vaporizer 12. The control panel may be a component of or separate from printed circuit board assembly 26. In either embodiment, the control panel is in electrical communication with printed circuit board assembly 26. The printed circuit board assembly 26 may be located below the flavor chambers to control the release of flavors. Flavor disk 14 selectively releases flavor depending on a control signal from the control panel. In some embodiments, the control signal is one or more control voltages delivered to printed circuit board assembly 26.

Each of chambers 24 a-f may have a respective corresponding mechanism for releasing flavor into a flow path of the vapor. For a given chamber, its respective corresponding mechanism for releasing flavor may cause flavor to be released from that chamber only in response to a control signal targeting that chamber. For example, the corresponding mechanism for releasing flavor from chamber 24a may cause flavor to be released from chamber 24a only when the control signal includes a unique aspect targeting chamber 24a. Similarly, the corresponding mechanism for releasing flavor from chamber 24b may cause flavor to be released from chamber 24b only when the control signal includes a unique aspect targeting chamber 24b. A control signal may target only one chamber or may target a plurality of chambers at the same time. In one exemplary operation, at a first time, the printed circuit board assembly 26 may receive a control signal that includes a unique aspect targeting chamber 24a but that lacks a unique aspect targeting chamber 24b. At this first time, the corresponding mechanism for releasing flavor from chamber 24a would be activated but the corresponding mechanism for releasing flavor from chamber 24b would not be activated. In another exemplary operation, at a different second time, the printed circuit board assembly 26 may receive a control signal that includes both a unique aspect targeting chamber 24a and a different unique aspect targeting chamber 24b. At this second time, both the corresponding mechanism for releasing flavor from chamber 24a and the corresponding mechanism for releasing flavor from chamber 24b would be activated. Exemplary operations above explicitly discuss a control signal with a unique aspect targeting only one of chambers 24 a-f and a control signal with unique aspects targeting only two of chambers 24 a-f. However printed circuit board assembly 26 may be configured to receive and respond to control signals that include unique aspects targeting any suitable combinations of chambers 24 a-f.

A mechanism for releasing flavor into a flow path of the vapor may come in any suitable form. In some embodiments, the printed circuit board assembly 26 may have one or more actuators for releasing flavoring. In some embodiments, the one or more actuators may be one or more piezoelectric actuators for releasing a liquid flavoring, similar to the operation of an inkjet printer. For example, printed circuit board assembly 26 may include six piezoelectric actuators, each respectively corresponding to, and configured to respectively release liquid flavoring from, one of chambers 24 a-f. Additionally or alternatively, in some embodiments, the printed circuit board assembly 26 may include one or more heat actuators that selectively heat one or more of chambers 24 a-f to release flavoring from the one or more of chambers 24 a-f. For example, a specific portion of printed circuit board assembly 26 may selectively heat chamber 24a, a different specific portion of circuit board assembly 26 may selectively heat chamber 24b, and so on. Additionally or alternatively, in some embodiments, printed circuit board assembly 26 may have one or more physical actuators for releasing flavor from one or more of chambers 24 a-f. For instance, an actuator of printed circuit board assembly 26 may selectively compress chamber 24a, forcing flavor from chamber 24a, a different actuator of printed circuit board assembly 26 may selectively compress chamber 24b, forcing flavor from chamber 24b, and so on.

Each of chambers 24 a-f may be sealed within flavor disk 14, with only flavor disk 14 being replaceable. For instance, in the embodiment of FIG. 2, each of chambers 24 a-f is encapsulated in a clear thermoplastic injection molded over the flavor chambers 24 a-f. In other embodiments, each of chambers 24 a-f may be individually replaceable to refill a flavor. In still other embodiments, chambers 24 a-f may be fixed, but respective passageways may provide respective access to chambers 24 a-f for refilling the flavors. The flavors within chambers 24 a-f may be liquid flavors or powder flavors.

Flavor disk 14 may be associated with a software application for controlling the release of flavor. The flavor disk 14 may work independently or coordinate with another device. A flavor disk 14 may communicate with an application on a device such as a smart phone. The smart phone may communicate to the user available flavors and flavor combinations. The smart phone may recognize that specific flavors and flavor combinations are available in association with a flavor disk 14 based upon characteristics of that flavor disk. In some embodiments, a user may purchase flavors separate from a flavor disk, such that flavor combinations are unlocked upon purchase using the application.

A user may use the application to select a flavor or flavor combination available in association with that flavor disk 14 and thereby cause the flavor disk 14 to release that available flavor or flavor combination. The user's selection of distinct flavors and flavor combinations may be communicated from the application to flavor disk 14 as distinct codes that the control panel of vaporizer 12 containing flavor disk 14 converts into control signals that printed circuit board assembly 26 uses to control release of one or more flavors. For example, in an exemplary operation, the user may view the application on a device such as a smart phone, see that a particular flavor is available in association with flavor disk 14, and select that flavor in the application using the smart phone. The smart phone may then communicate the distinct code for that flavor to the control panel of vaporizer 12 containing flavor disk 14, and printed circuit board assembly 26 may convert the code into a control signal with a unique aspect targeting the release of the selected flavor from its chamber. In another exemplary operation, the user may view the application on a device such as a smart phone, see that a particular flavor combination is available in association with flavor disk 14, and select that flavor combination in the application using the smart phone. The smart phone may then communicate the distinct code for that flavor combination to the control panel of vaporizer 12 containing flavor disk 14, and printed circuit board assembly 26 may convert the code into a control signal with unique aspects targeting the release from their respective chambers of the various flavors that form the selected flavor combination.

A user may inhale the one or more flavors independently or use the one or more flavors as an additive for a tobacco or e-liquid vaporizer. For example, vaporizer 10 of FIG. 1 may provide an inhalation path without requiring the production of vapor. Or vaporizer 12 may produce vapor which is then mixed with the flavoring.

Figure 4:
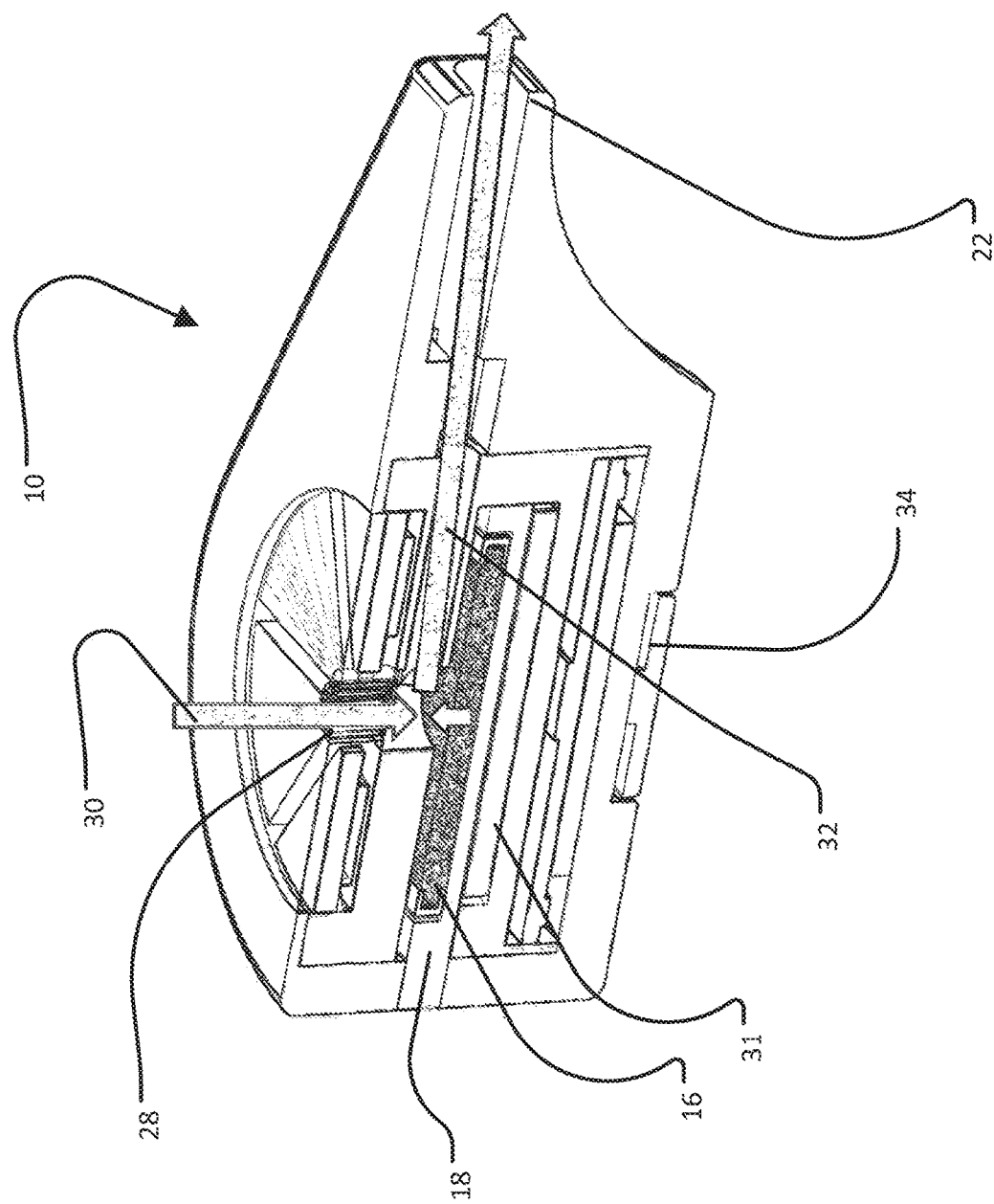
FIG. 4 illustrates a sectional view of an embodiment of a vaporizer assembly.

FIG. 4 illustrates a cross section of vaporizer assembly 10 illustrating its operation. The central portion of flavor disk 14 has a porous center 28 for passing a fluid 30, such as air, through flavor disk 14. Each flavor chamber is in fluid communication with porous center 28 so that flavor from flavor disk 14 may be mixed with the fluid as it passes through the flavor disk.

Below flavor disk 14, tray 18 stores vaporizer product 16 that produces vapor when exposed to heat, atomization conditions or other vapor source conditions. Vapor Source 31 is positioned below tray 18 and vaporizer product 16. Exemplary vapor sources include an atomizer, a heater, or other known vapor source, and any combination(s) thereof. In certain embodiments vapor source 31 is a heater, and provides heat on demand to produce vapor from vapor product 16 when desired. The vapor travels upward into fluid (or air) channel 32 where it mixes with any flavor added to the incoming fluid 30 from porous center 28 of flavor disk 14. If "flavor only" is selected, heater 31 is not activated and no vapor is produced. Instead, the flavored fluid (or air) passes through fluid channel 32 without mixing with vapor. A user inhales flavored fluid through mouthpiece 22 which is in fluid communication with fluid channel 32. If heat button 34 is pressed, heater 31 is activated and vapor is produced, providing flavored vapor at the mouthpiece 22.

The descriptions set forth above are meant to be illustrative and not limiting. Various modifications of the disclosure, in addition to those described herein, will be apparent to those skilled in the art from the foregoing description. Such modifications are also intended to fall within the scope of the concepts described herein. The disclosures of each patent, patent application and publication cited or described in this document are hereby incorporated herein by reference, in their entireties.

The foregoing description of possible implementations consistent with the present disclosure does not represent a comprehensive list of all such implementations or all variations of the implementations described. The description of some implementation should not be construed as an intent to exclude other implementations. For example, artisans will understand how to implement the disclosure in many other ways, using equivalents and alternatives that do not depart from the scope of the disclosure. Moreover, unless indicated to the contrary in the preceding description, none of the components described in the implementations are essential to the disclosure. It is thus intended that the embodiments disclosed in the specification be considered as illustrative, with a true scope and spirit of the disclosure being indicated by the following claims.

The invention claimed is:

1. A flavor disk for a vaporizer, the flavor disk comprising:
 a plurality of chambers, each chamber storing a flavor component;
 an actuator for each chamber, the actuator configured to selectively release a portion of the flavor component from the chamber;
 a flow path extending through the flavor disk and positioned to receive and direct incoming fluid as it enters and passes through the flavor disk, the flow path being in fluid communication with each chamber to thereby allow the portion of the flavor component received within the flow path to mix with the incoming fluid as the incoming fluid passes through the flow path; and
 control circuitry to selectively actuate the actuator.

2. The flavor disk according to claim 1, wherein the plurality of chambers comprises 2 to 6 chambers.

3. The flavor disk according to claim 1, wherein the actuator is a piezoelectric actuator.

4. The flavor disk according to claim 1, wherein the actuator is a heat actuator.

5. The flavor disk according to claim 1, wherein the chamber has a passageway suitable for refilling the chamber with the flavor component.

6. The flavor disk according to claim 1, further comprising a printed circuit board assembly.

7. The flavor disk according to claim 6, wherein the printed circuit board assembly is configured to receive and respond to a control signal targeting a chamber or any suitable combination of the chambers.

8. A vaporizer assembly comprising:
 a flavor disk comprising:
  a plurality of chambers, each chamber storing a flavor component,
  an actuator for each chamber, the actuator configured to selectively release a portion of the flavor component from the chamber,
  a flow path positioned to receive the portion of the flavor component and mix the portion of the flavor component with incoming fluid, and
  control circuitry to selectively actuate the actuator; and
 a vaporizer comprising:
  a first cavity configured to receive the flavor disk,
  a slot positioned beneath and proximate to the first cavity, the slot being configured to receive a tray that includes vapor product,
  a vapor source positioned beneath and proximate to the slot, the vapor source configured to vaporize the vapor product into vapor, and
  a fluid channel that is in fluid communication with the flow path of the flavor disk, the fluid channel being configured to receive a mixture of the portion of the flavor component and incoming fluid from the flow path and direct the mixture through the vaporizer for inhalation.

9. The vaporizer assembly according to claim 8, wherein the vaporizer further comprises the tray.

10. The vaporizer assembly according to claim 8, wherein the flavor disk is detachable from the vaporizer.

11. The vaporizer assembly according to claim 8, wherein the flavor disk is flavor-reloadable.

12. The vaporizer assembly according to claim 8, wherein the vaporizer further comprises a mouthpiece.

13. The vaporizer assembly according to claim 12, wherein the mouthpiece is configured to connect to a mouthpiece extension.

14. A flavor disk for a vaporizer, the flavor disk comprising:
 a body extending from a top surface to a bottom surface, the body having a flow path extending between the top and bottom surfaces and configured to allow and direct incoming fluid to enter and pass through the flavor disk;
a plurality of chambers disposed within the body proximate to the top surface and in fluid communication with the flow path, each chamber configured to selectively store a flavor component therein; and
a printed circuit board assembly disposed within the body and positioned adjacent to the plurality of chambers, the printed circuit board assembly configured to control the release of the flavor component from each respective chamber; and
control circuitry configured to selectively transmit at least one control signal to the printed board assembly to cause a release of at least a portion of the flavor component from at least one chamber.

15. The flavor disk according to claim 14, wherein the printed circuit board assembly comprises a release mechanism associated with each chamber, the release mechanism being configured to selectively release at least a portion of the flavor component from its respective chamber to allow the released portion of the flavor component to enter the flow path and mix with the incoming fluid passing therethrough.

* * * * *